(12) United States Patent
Singh

(10) Patent No.: US 12,419,981 B2
(45) Date of Patent: Sep. 23, 2025

(54) TENNIS BALLS SANITIZING MACHINE

(71) Applicant: Shashwat Singh, Frisco, TX (US)

(72) Inventor: Shashwat Singh, Frisco, TX (US)

( * ) Notice: Subject to any disclaimer, the term of this patent is extended or adjusted under 35 U.S.C. 154(b) by 1038 days.

(21) Appl. No.: 17/325,113

(22) Filed: May 19, 2021

(65) Prior Publication Data
US 2022/0370664 A1    Nov. 24, 2022

(51) Int. Cl.
| | |
|---|---|
| *B08B 1/00* | (2024.01) |
| *A61L 2/22* | (2006.01) |
| *A61L 2/26* | (2006.01) |
| *B08B 3/00* | (2006.01) |
| *A63B 102/02* | (2015.01) |

(52) U.S. Cl.
CPC .............. *A61L 2/22* (2013.01); *A61L 2/26* (2013.01); *A61L 2202/122* (2013.01); *A61L 2202/14* (2013.01); *A61L 2202/15* (2013.01); *A61L 2202/16* (2013.01); *A63B 2102/02* (2015.10)

(58) Field of Classification Search
CPC ......... A61L 2/22; A61L 2/26; A63B 2102/02; A63B 47/04; B08B 3/02
USPC .......... 15/104.94, 21 A, 104.92, 160, 210 R; 134/57 R, 72, 107–108, 111; 219/314
See application file for complete search history.

(56) References Cited

U.S. PATENT DOCUMENTS

| | | | | |
|---|---|---|---|---|
| 4,805,649 A | * | 2/1989 | Nezworski | ................ B08B 9/30 134/107 |
| 5,842,916 A | * | 12/1998 | Gerrity | ..................... B07B 1/24 453/57 |

\* cited by examiner

*Primary Examiner* — Monzer R Chorbaji

(57) ABSTRACT

COVID-19 and many other infectious diseases like Flu can spread through by touch. Tennis player exchange the same balls multiple times during the practice or game. For student's safety schools and colleges currently sanitize the balls manually which is a tedious and time taking job. This invention sanitizes the bunch of tennis balls in one go with the push of a buttons and a Knob which control the speed of motor vibration.

2 Claims, 3 Drawing Sheets

TENNIS BALLS SANITIZING MACHINE

BACKGROUND

COVID-19 has spread to almost every country in the world and we have taken bunch of precautions to slow down its spread. We sanitize many things including Tennis balls. Currently we have the various sanitizers available in the market but none of them is designed to sanitize the Tennis balls in an automated way. COVID-19 or other infectious diseases like Flu might spread through the use of same Tennis balls by many people during the game or practice. One of the solution is to sanitize each Tennis balls manually after each use which is a tedious job. Schools and colleges currently sanitizes the balls manually for student's safety therefore a need exists for a novel Tennis Balls sanitizing machine.

BRIEF SUMMARY OF THE INVENTION

The present invention comprises of a platform with a vibrating base. The base holds the tennis balls. A separate part would have a sanitizer which would blow the mist towards the base. Tennis balls will get the mist. Vibration will ensure that every Tennis balls get the sanitizing mist as vibration makes ball rotate. Rolling balls gets mist on its all surface and get sanitized. The vibration base is controlled using the knob. Sanitizer can be triggered using the sensor or with a push of a button. These both units are portable and detached to each other but work in harmony. This new machine can sanitize bunch of Tennis balls in one go in an automated fashion. School and colleges or tennis facilities don't need to sanitize the balls manually and they can use this machine to sanitize bunch of balls in one go.

DETAILED DESCRIPTION OF THE INVENTION

Reference will now be made in detail to certain embodiments of the invention, examples of which are illustrated in the accompanying drawings. While the invention will be described in reference to these figures and certain implementations and examples of the embodiments, it will be understood that such implementations and examples are not intended to limit the invention. To the contrary, the invention is intended to cover alternatives, modifications, and equivalents that are included within the spirit and scope of the invention as defined by the claims. In the following disclosure, specific details are given to provide a thorough understanding of the invention. References to various features of the "invention" throughout this document do not mean that all claimed embodiments or methods must include the referenced features. It will be apparent to one skilled in the art that the present invention may be practiced without these specific details or features.

This invention is able to sanitize bunch of tennis balls in one go with the help of vibration and disinfecting mist.

Figure 1:
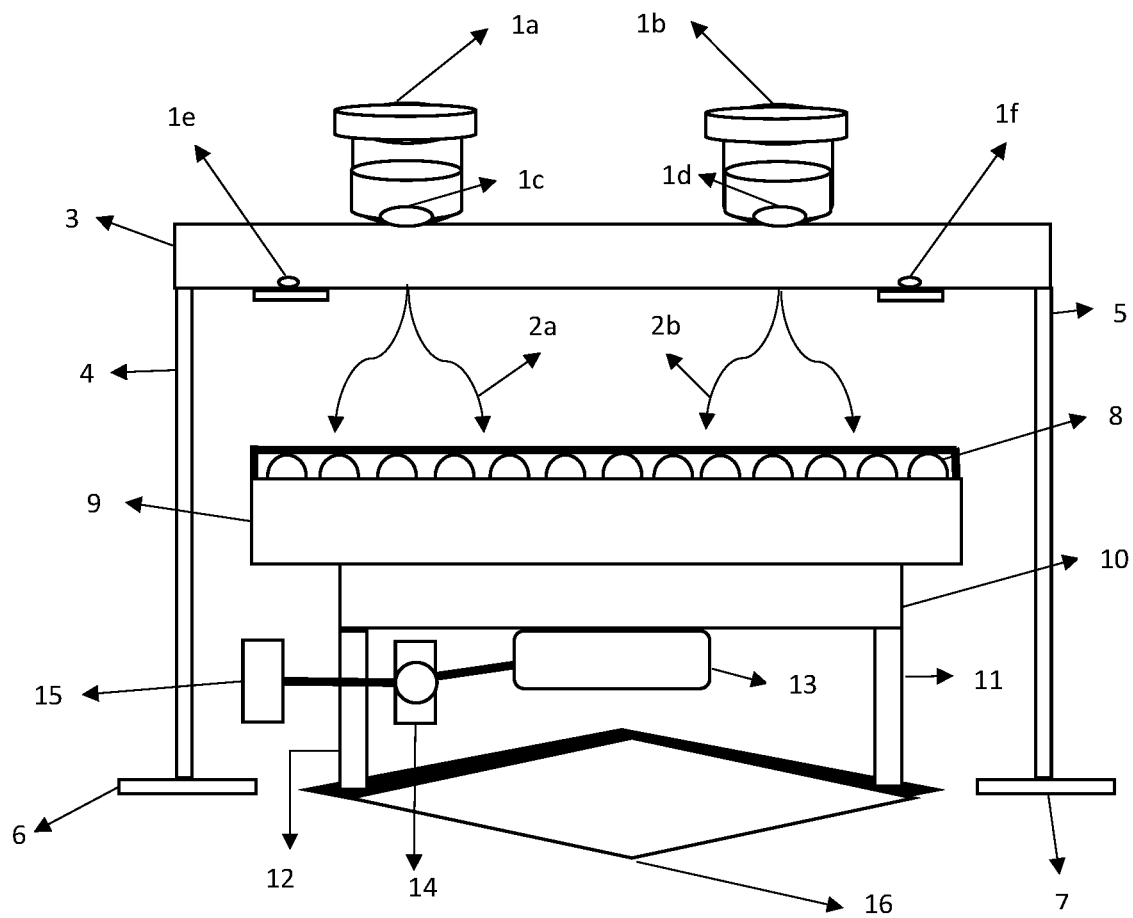

FIG. 1 presents the front view of the machine where number 1a and 1b represents two or more containers which hold the sanitizing liquids. The bottom of the container which is represented by FIGS. 1, 1c and 1d has a mist plate which on connecting to USB port or battery produces the mist. Mist plate should be firmly attached to the container at the bottom. The bottom of the container should have a hole so that liquid keep going to plate which in turn would make the mist which goes to balls.

FIGS. 1, 1e and 1f represents mist circuit which is attached to the rectangular rod under the bottom part with on and off switch. The on and off switch helps to turn on or off the mist. The mist circuit is attached to the bottom mist plate by an electrical wire.

Figure 2:
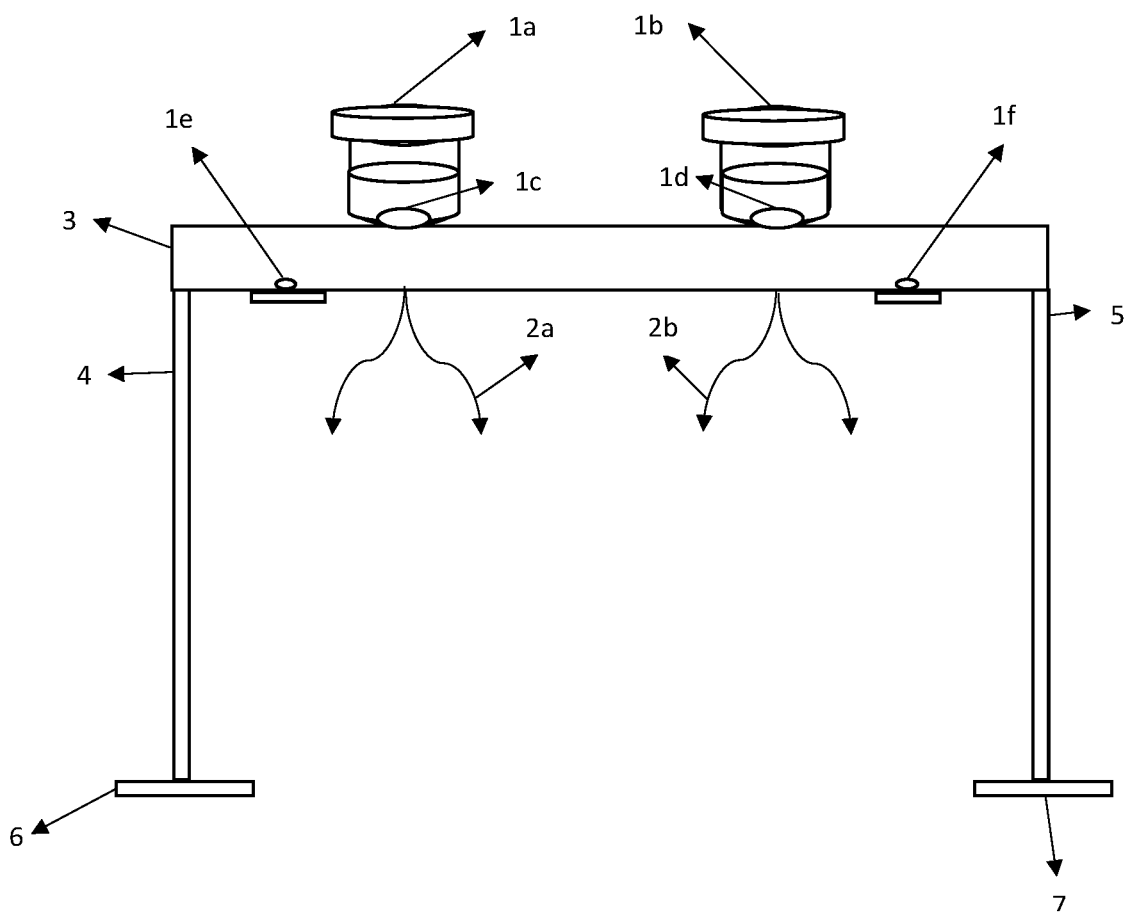
Figure 3:
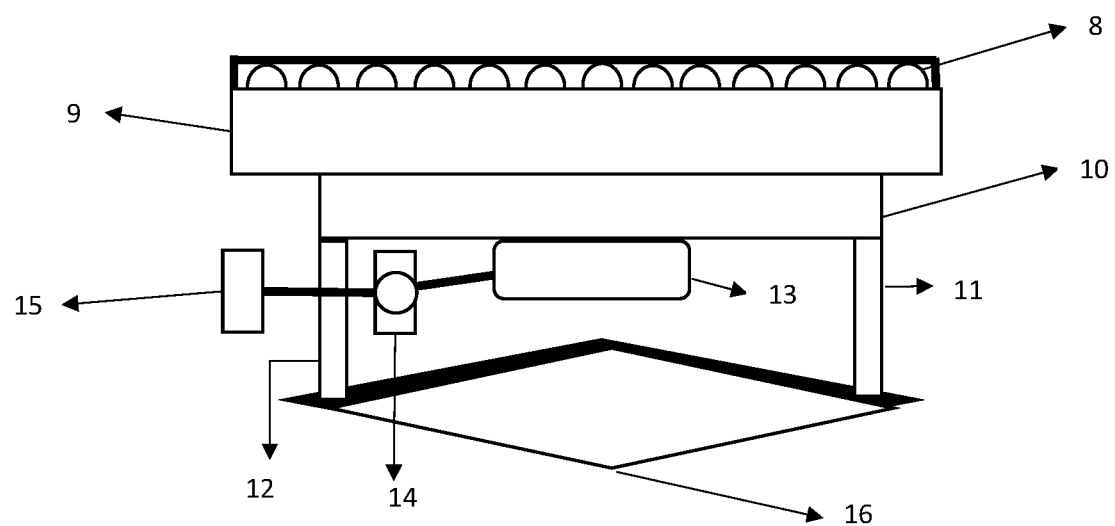

FIGS. 1, 2a and 2b represents the mist going to the box containing the tennis balls. Mist is shown by the arrow. During the run time the mist can be seen inside the box as box has a depth and is covered by the sides which holds the mist and applies to Tennis balls.

FIG. 1, 3-7 represents the structure holding the mist container which is self-standing structure. It has two pillars which rest on square, circular or oval base on each side for stability. The two pillars are connected by a rectangular shaped rod. The upper surface of rod holds the two or more sanitizing liquids containers and the bottom of the rod contains the mist circuit and a on and off switch.

FIG. 1, 8 represents tennis balls that needs to be sanitized. Balls should be placed such that one layer is formed for more effective sanitizing. The balls should not be on the top of other ball. One layer of balls helps balls to rotate easily which ensures balls complete surface is sanitized.

FIG. 1, 9 represents a box which is attached to the top of the table base. This box contains the tennis balls that needs to be sanitized. This box has a hole on each side so that the whole unit can be lift or to move from one place to another. Box can have handles as well to carry it from one place to another.

FIG. 1, 10-12 represents a table which holds the vibrating motor and box containing the tennis balls. The Box is attached to table and box contains the tennis balls. Underneath the table, a vibrating motor is attached which creates the vibration. Vibration passes to box and to balls as box is attached to table. The motor and box are attached with nuts and bolts so that they can withstand the vibration and don't fall off.

FIG. 1, 13 represents a vibrator motor. Vibration motor creates vibration to box which in turns vibrates the ball. Ball starts rolling because of vibration which helps to sanitize the 360 degree surface of balls. Vibration motor vibration needs to be controlled because excessive vibration makes ball jumps.

FIG. 1, 14 represents a knob controlled electric current. Knob controls the amount of electric which passes to motor which in turns reduces or increases the vibration of the motor. This helps to ensure enough vibration is created to roll the balls.

FIG. 1, 15 represents power outlet to attach vibration motor to outlet. Vibration motor is ac current driven and needs power from any standard power outlet.

FIG. 1, 16 represents double layer vibration dampener. Vibration to box causes the whole unit to vibrate and hence unit starts to move and at high vibration it starts to run away. Vibration dampener reduces the vibration and helps machine stay at one place. This makes machine portable, other solution is to screw the unit to a table or floor.

To sanitize the balls the following steps should be performed:—

Step 1:—Put enough tennis balls in the box so that it forms a single layer. Based on need the box size can be increased and accordingly the sanitizing liquid mist makers. Balls can touch each other side by side but don't force the additional balls once single layer is formed. Balls should not be sitting on the top of another ball.

Step 2: Connect the vibration motor to power outlet and turn the knob slowly so that vibration starts. Once vibration starts turn the knob more so that balls starts rolling. Make sure all balls starts rolling.

Step 3: Turn on the mists, ensure mist starts going towards the balls. Run time of the mist should be as per sanitizing liquid specifications. Mist should be run for the period of time recommended by sanitizing liquid specification to kill the pathogen or viruses. Once done mist should be turned off. You should see the mist layer inside the box during run time.

Step 4: Turn off the mists, and then the vibration motor and remove the sanitized balls. Put the new sets of balls in the box and repeat the steps 1 through 3 again.

BRIEF DESCRIPTIONS OF THE DRAWING

FIG. 1 has all components working in harmony. Details of each component is given below:—

- 1*a* represents container having the sanitizer liquid. Containers can be two or more in numbers. They can be of different sizes.
- 1*b* represents container having the sanitizer liquid. Containers can be two or more in numbers. They can be of different sizes.
- 1*c* represents mist sprayer plate which is attached to left liquid container base.
- 1*d* represents mist sprayer plate which is attached to right liquid container base.
- 1*e* represents mist circuit with on and off switch which is attached to left mist sprayer plate by wire.
- 1*f* represents mist circuit with on and off switch which is attached to right mist sprayer plate by wire.
- 2*a* represents mist coming out from the left sprayer container.
- 2*b* represents mist coming out from the right sprayer container.
- 3 represents rectangular top which holds the containers.
- 4 represents left pillar or stand which are attached to rectangular top and to a square, oval or circular base on other end.
- 5 represents right pillar or stand which are attached to rectangular top and to a square, oval or circular base on other end.
- 6 represents left square, oval or circular base which is attached to pillars or stand.
- 7 represents right square, oval or circular base which is attached to pillars or stand.
- 8 represents Tennis balls that needs to be sanitized.
- 9 represents a rectangular box which is open from the top is attached to the top of the table base.
- 10 represents a table top which holds the vibrating motor underneath and box containing the tennis balls.
- 11 represents Table right leg.
- 12 represents Table left leg.
- 13 represents a vibrator motor. Vibration motor creates vibration to box which in turns vibrates the ball.
- 14 represents a knob controlled electric circuit. Knob controls the electric current amount which in turns reduces or increases the vibration of the motor. This helps to ensure enough vibration is created to roll the balls.
- 15 represents power outlet to attach vibration motor to outlet.
- 16 represents vibration dampener. Vibration to box causes the whole unit to vibrate and hence move and at high vibration it starts to run away. Vibration dampener reduces the vibration and helps machine stay at one place. This makes machine portable, other solution is to screw the unit to a table or floor.

FIG. 2 depicts the whole Sanitizing unit which comprises of 1*a*, 1*b*, 1*c*, 1*d*, 1*e*, 1*f*, 2*a*, 2*b*, 3, 4, 5, 6 and 7. It has a self-standing structure holding the containers and sanitizing plates and circuits to create the mist.

FIG. 3 depicts vibrator unit which comprises of 8-16. It has a self-standing structure or stool which holds the balls and Vibration motor to rotate the tennis balls.

Some embodiments of the present invention are illustrated as an example and are not limited by the figures of the accompanying drawings. FIG. 1 depicts the front view of the present invention. The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

What is claimed is:

1. Tennis ball Sanitizing machine which sanitizes tennis balls with the help of vibration and disinfecting mist without soaking the ball, comprising: a housing having a dampener which dampens the vibration; a structure that sits on the dampener, wherein the structure has a flat rectangular or oval or circular table top having two legs, which has an attached box containing the tennis balls that needs to be sanitized; the attached box contains a single layer of tennis balls, which helps the balls rotate easily and ensures that the entire surface of each ball is sanitized; a vibration motor underneath the tabletop, configured to create the necessary vibration to rotate the tennis balls; The motor and the attached box are secured with nuts and bolts to withstand the vibration and prevent them from falling off and vibration rotates the tennis balls, helping to sanitize the entire 360-degree surface of each ball; the attached box with a handle to carry the housing; an external vibration control knob resides external to the housing which controls the vibration of the motor by controling the electric current flowing to the motor, which in turn allowing it to get sufficient vibration to rotate the balls.

2. The tennis balls sanitizing machine of claim 1, further comprises a separate sanitizing unit with two pillars that are attached to a square, circular, or oval base on each side to make it stand on its own, wherein the pillars on the other end are attached by a horizontal rectangular rod which houses two or more vertical standing containers on the top which holds the sanitizing liquids; containers base having mist plate attached to create the mist; mist circuit attaching to the bottom of the rectangular rod outside of the container with on and off switch to turn on or off the mists; the mist circuit is attached to the bottom mist plate by an electrical wire; the bottom of the containers has a hole, allowing liquid to flow onto the plate, which then generates mist that reaches the balls; the mist should be applied for the duration recommended by the sanitizing liquid's specifications to effectively kill pathogens or viruses.

* * * * *